United States Patent
Velez Wiesner

(10) Patent No.: US 10,624,728 B2
(45) Date of Patent: Apr. 21, 2020

(54) EXTERNAL MALE INCONTINENCE CLAMP

(71) Applicant: Juan Felipe Velez Wiesner, Medellin (CO)

(72) Inventor: Juan Felipe Velez Wiesner, Medellin (CO)

( * ) Notice: Subject to any disclaimer, the term of this patent is extended or adjusted under 35 U.S.C. 154(b) by 595 days.

(21) Appl. No.: 15/253,051

(22) Filed: Aug. 31, 2016

(65) Prior Publication Data

US 2018/0055617 A1 Mar. 1, 2018

(51) Int. Cl.
*A61F 2/00* (2006.01)

(52) U.S. Cl.
CPC .... *A61F 2/0054* (2013.01); *A61F 2220/0091* (2013.01)

(58) Field of Classification Search
CPC .. A61F 2220/0091; A61F 2/0054; A61F 2/00; A61F 2/0004; A61F 2/0009; A61F 2/0013; A61F 2/0018; A61F 2/0031; Y10S 128/25; A61B 17/122; A61B 17/1322
USPC ......... 128/885, DIG. 25, 842; 606/157, 151, 606/201; 600/29; D24/143
See application file for complete search history.

(56) References Cited

U.S. PATENT DOCUMENTS

| 3,203,421 | A | * | 8/1965 | Bialick | A61F 2/0054 128/885 |
|---|---|---|---|---|---|
| 5,571,125 | A | * | 11/1996 | Chadwick | A61B 17/122 128/DIG. 25 |
| 5,842,968 | A | * | 12/1998 | Johnson | A61F 2/0054 600/38 |
| 2004/0129277 | A1 | * | 7/2004 | Parkes | A61F 2/0054 128/885 |
| 2005/0267324 | A1 | * | 12/2005 | Timm | A61F 2/0036 600/30 |
| 2014/0041672 | A1 | * | 2/2014 | Garc a Berruezo | A61F 2/0054 128/885 |

OTHER PUBLICATIONS

Wiesner Incontinence Clamp | Confidence & Comfort all day long! (n.d.). Retrieved Aug. 31, 2016, from http://www.wiesnerhealth.com/.

* cited by examiner

*Primary Examiner* — Anna K Kinsaul
*Assistant Examiner* — Caitlin A Carreiro
(74) *Attorney, Agent, or Firm* — Dunlap Bennett & Ludwig PLLC

(57) ABSTRACT

An incontinence clamp is provided. The incontinence clamp includes an upper clamp arm and a lower clamp arm. Each of the upper and lower clamp arms include a first end, a second end, an inner surface and an outer surface. The inner surfaces face each other. A hinge pivotally connects the first ends of the upper and lower clamp arms together. An upper guide is coupled to the inner surface of the upper clamp arm and a lower guide is coupled to the inner surface of the lower clamp arm. A connector releasably connects the second ends of the upper clamp arm and the lower clamp arm together.

9 Claims, 4 Drawing Sheets

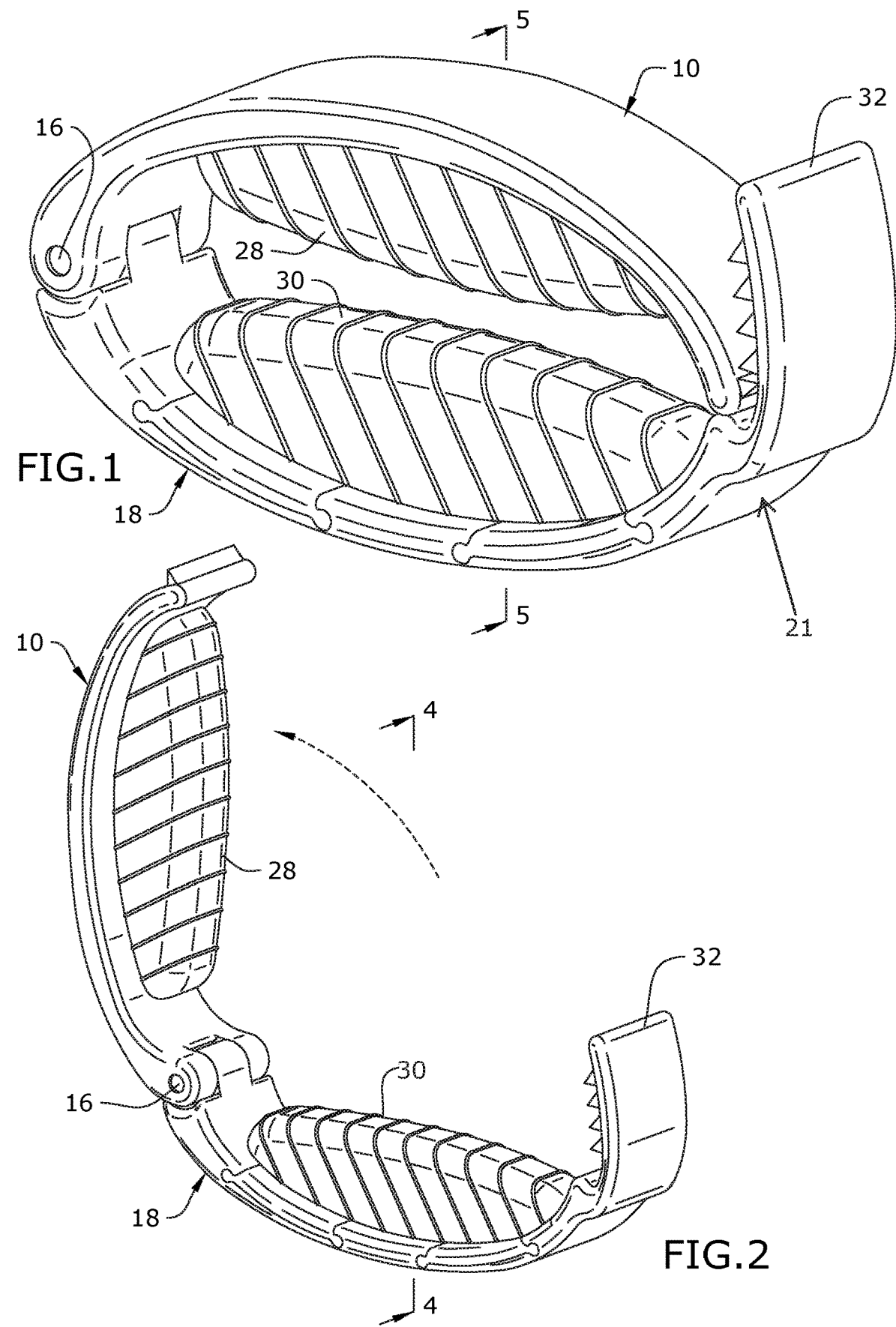

EXTERNAL MALE INCONTINENCE CLAMP

BACKGROUND OF THE INVENTION

The present invention relates to incontinence prevention and, more particularly, to an external male incontinence clamp.

Incontinence is a problem encountered by many men and is more common among geriatrics. While the cause of male incontinence may have a variety of different reasons, the uncontrolled and undesired passage of urine is a significant problem resulting in embarrassment, restriction of activities and depression.

While adult diapers are one solution to the problem, they are bulky, retain the moisture, and are embarrassing and difficult for some aging men to handle. Other incontinence clamps have been developed over the years, but since anatomies is different between individuals, it is difficult to create a good fit between the device and the penis. This causes the devices to be extremely uncomfortable and ineffective.

Most of the incontinence clamps developed use foam pads as the interface material between the device and the skin. This creates irritation and swelling of the skin. When the foam collects urine it is very difficult to clean and device smells bad. Some other clamps include Polivynilsiloxane pads. This material is much better than foam but given the properties of the material, it will release natural oil which acts as lubricant and causes the clamp to slip out of position.

As can be seen, there is a need for an improved male incontinence clamp which retains on the penis during everyday activities, that adapts to the anatomy of the patient, that is easy for older men to use and provides control of incontinence without causing irritation or swelling of the tissue.

SUMMARY OF THE INVENTION

In one aspect of the present invention, an incontinence clamp comprises: an upper clamp arm comprising a first end, a second end, an inner surface and an outer surface; a lower clamp comprising a first end, a second end, an inner surface and an outer surface; a hinge pivotably connecting the first end of the upper clamp arm to the first end of the lower clamp; an upper guide coupled to the inner surface of the upper clamp arm and comprising a curved concave inner surface; a lower guide coupled to the inner surface of the lower clamp and comprising a first side portion, a second side portion and a middle portion disposed in between the first side portion and the second side portion, wherein the middle portion comprises a curved convex portion protruding towards the upper clamp arm; and a connector releasably connecting the second end of the upper clamp arm to the second end of the lower clamp arm.

These and other features, aspects and advantages of the present invention will become better understood with reference to the following drawings, description and claims.

BRIEF DESCRIPTION OF THE DRAWINGS

FIG. 1 is a perspective view of an embodiment of the present invention shown in a closed configuration;

FIG. 2 is a perspective view of an embodiment of the present invention shown in an open configuration;

DETAILED DESCRIPTION OF THE INVENTION

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

The present invention includes an external male incontinence clamp. When the clamp is placed on the penis, the device occludes the urethra while promoting blood circulation. The clamp of the present invention includes guides that adapt the user anatomy in shape and size. The material used is biocompatible, does not cause irritation or swelling, promotes a good perspiration of the skin and does not slip off of the penis.

Figure 3:
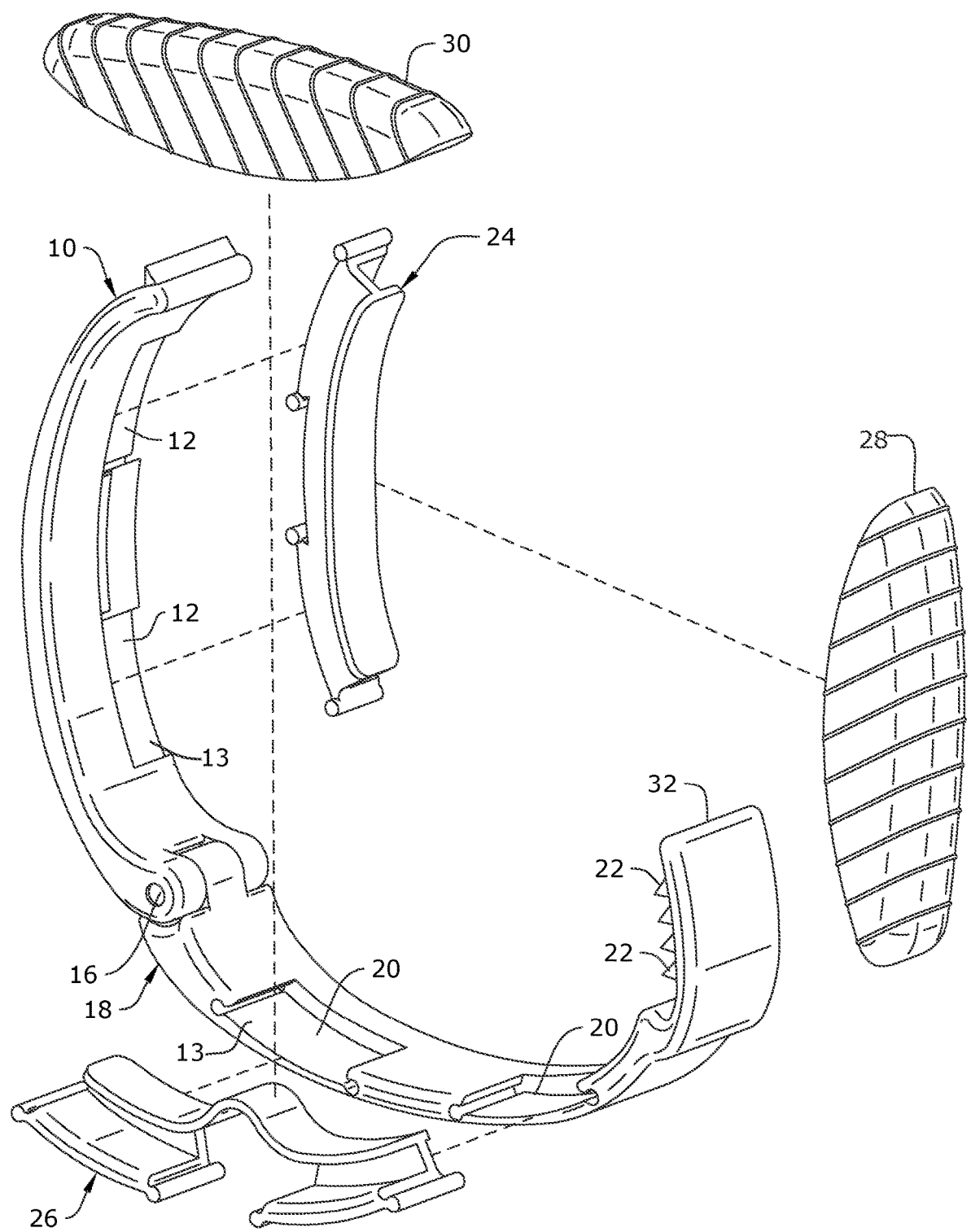
FIG. 3 is an exploded view of an embodiment of the present invention.
Figure 4:
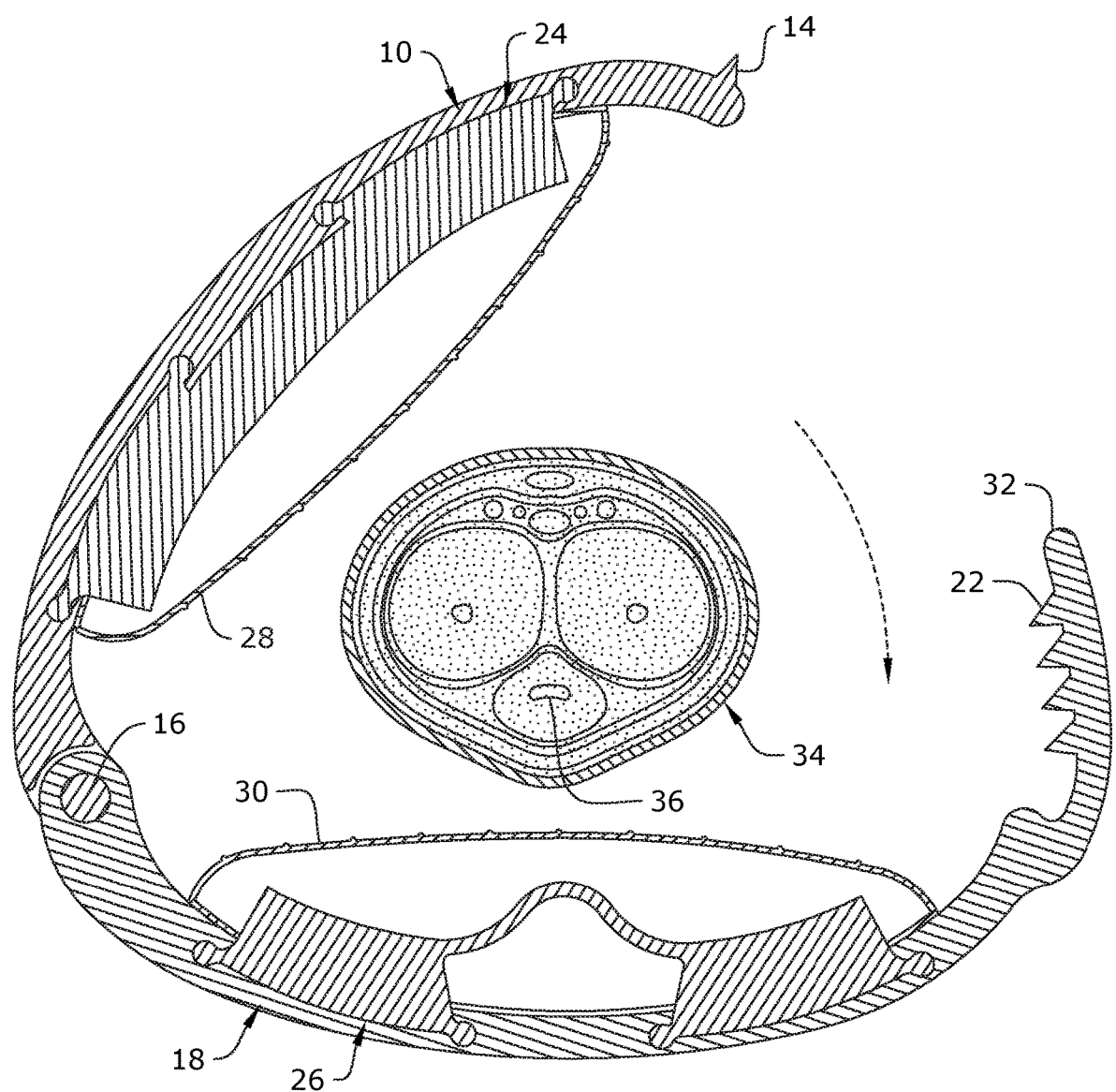
FIG. 4 is a section view of the present invention taken along line 4-4 in FIG. 2.
Figure 5:
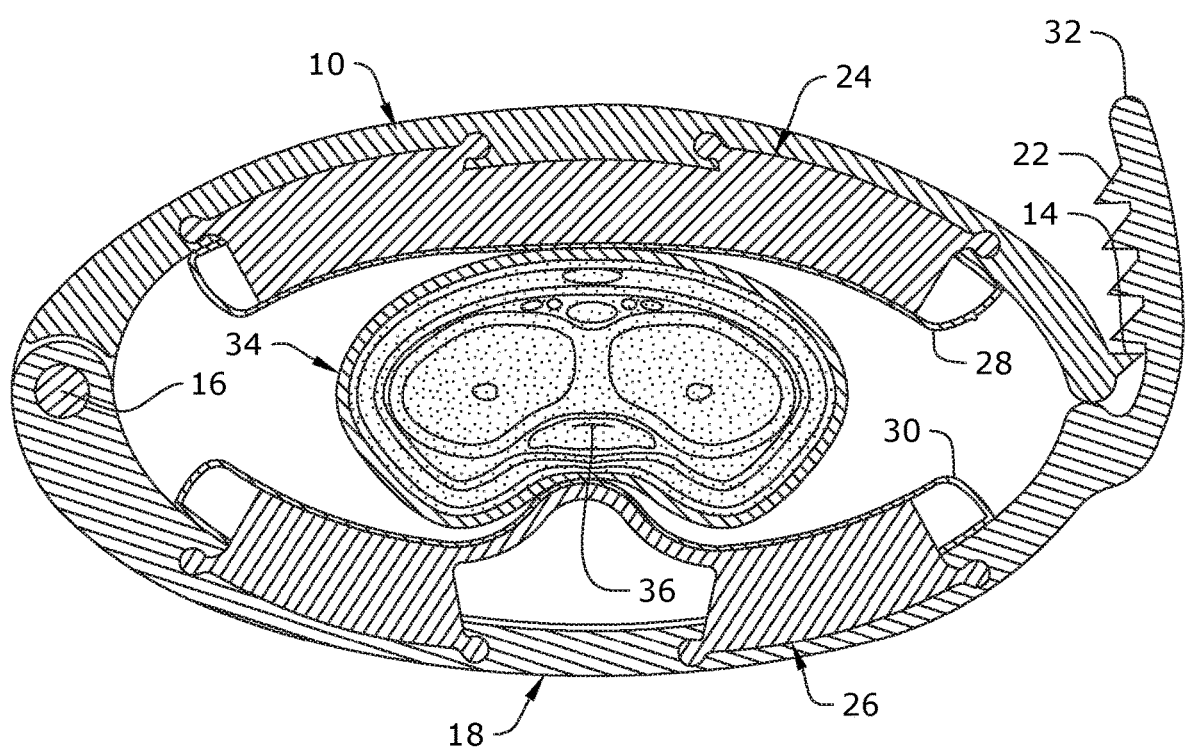
FIG. 5 is a section detail view of the present invention taken along line 5-5 in FIG. 1.

Referring to FIGS. 1 through 5, the present invention includes an incontinence clamp. The incontinence clamp includes an upper clamp arm 10 and a lower clamp arm 18. Each of the upper and lower clamp arms 10, 18 include a first end, a second end, a first side edge, a second side edge, an inner surface and an outer surface. The inner surfaces face each other. A hinge 16 pivotally connects the first ends of the upper and lower clamp arms 10, 18 together. An upper guide 24 is coupled to the inner surface of the upper clamp arm 10 and a lower guide 26 is coupled to the inner surface of the lower clamp arm 18. A connector 21 releasably connects the second ends of the upper clamp arm 10 and the lower clamp arm 18 together.

The upper guide 24 and lower guide 26 contours to the penis 34 and applies pressure to the urethra 36, preventing incontinence. The upper guide 24 includes a curved concave inner surface. The lower guide 26 includes a first side portion, a second side portion and a middle portion disposed in between the first side portion and the second side portion. The middle portion includes a curved convex portion protruding towards the upper clamp arm 10. The first side portion and the second side portion may each include a curved concave inner surface curving in the opposite direction of the middle portion. The upper guide 24 and the lower guide 26 may be formed of a rigid polymer to provide appropriate pressure to the penis 34. For example, the rigid polymer is acrylonitrile butadiene styrene.

In certain embodiments, the upper guide 24 and the lower guide 26 are releasably attached to the inner surface of the upper clamp arm 10 and lower clamp arm 18 respectively. Since the upper and lower guides 24, 26 may be removable, a user may replace the guides 24, 26 depending on the size of the penis 34. In such embodiments, a slot 12 may be formed on the inner surface of the upper clamp arm 10. The slot 12 includes an entrance 13 leading into the slot 12 defined on the first side edge. The upper clamp guide 24 includes a ridge releasably retained within the slot 12 by sliding laterally through the entrance 13 and towards the second side edge. A slot 20 may be formed on the inner surface of the lower clamp arm 18. The slot 20 on the lower clamp arm 18 may also include an entrance 13 leading into the slot 12 defined on the first side edge. The lower clamp guide 26 includes a ridge releasably retained within the slot 20 by sliding laterally through the entrance 13 and towards the second side edge.

The present invention may further include a padding 28, 30. An upper padding 28 may be secured to the upper clamp arm 10 and a lower padding 30 may be secured to the lower clamp arm 18. The padding 28, 30 may be in the shape of a cover and is sized to releasably secure over the upper and lower guides 24, 26 respectively. The padding 28, 30 may include ridges formed on an outer surface to prevent slipping. The padding 28, 30 adds comfort to the present invention. The padding 28, 30 may be made of a thermoplastic elastomer.

The connector 21 of the present invention may include a plurality of connecting positions. Each of the connecting positions forms a different internal diameter of the incontinence clamp. For example, one of the second ends includes an interlocking tooth 14 and the other of the second ends includes a plurality of interlocking teeth 22. The interlocking tooth 14 is secured in between the plurality of interlocking teeth 22, releasably connecting the second ends together. As illustrated in the Figures, the interlocking tooth 14 may protrude from the outer surface of the upper clamp arm 10. The plurality of interlocking teeth 22 may protrude from an inner surface of a tooth tab 32 extending from the second end of the lower clamp arm 18. Pressing the clamp arms 10, 18 together releasably retains the second end of the upper clamp arm 10 to the second end of the lower clamp arm 18. The interlocking tooth 14 disposed in between different interlocking teeth 22 adjusts the diameter of the incontinence clamp.

In use, the users select the guides that better correspond to their penis shape and size. Then the user assembles the guides into the clamp by sliding the guides in the slots formed in the inner surface. After assembling the guides, the user assembles the pads over the guides. Once the pads are assembled, the user opens the incontinence clamp by releasing the catch and lifting up the top arm. The user may then place the penis between the pads with the incontinence clamp about halfway down the shaft. Latch the incontinence clamp to compress the urethra at the level that's comfortable to the user. The bottom part of the clamp is designed to concentrate the pressure in the urethra while providing room to the corpora cavernosa to move on the sides. The top part of the clamp is designed to promote a correct blood circulation and sensation, enabling the dorsal arteries, veins and nerve to be in a pressure significantly lower than the applied in the urethra. Given the variety of guides and pressure levels of the clamp, the adaptation between the device and the penis is much more effective, reliable and healthier for the patient. The pads with ridges permit the correct skin perspiration and prevent slippage. Due to the flexibility of the material, the pads provide comfort to the user.

It should be understood, of course, that the foregoing relates to exemplary embodiments of the invention and that modifications may be made without departing from the spirit and scope of the invention as set forth in the following claims.

What is claimed is:

1. An incontinence clamp comprising:
    an upper clamp arm comprising a first end, a second end, an inner surface and an outer surface;
    a lower clamp arm comprising a first end, a second end, an inner surface, an outer surface, a first side edge, and a second side edge, wherein the lower clamp arm comprises a lower slot disposed on the inner surface and comprising an entrance leading into the lower slot defined on the first side edge;
    a hinge pivotably connecting the first end of the upper clamp arm to the first end of the lower clamp arm;
    an upper guide coupled to the inner surface of the upper clamp arm, wherein the upper guide further comprises a curved concave inner surface;
    a lower guide comprising a ridge releasably retained within the lower slot by sliding laterally through the entrance and towards the second side edge, wherein the lower guide further comprises a first side portion, a second side portion and a middle portion disposed in between the first side portion and the second side portion, wherein the middle portion comprises a curved convex portion protruding towards the upper clamp arm; and
    a connector releasably connecting the second end of the upper clamp arm to the second end of the lower clamp arm.

2. The incontinence clamp of claim 1, further comprising an upper padding releasably secured over the upper guide and a lower padding releasably secured over the lower guide.

3. The incontinence clamp of claim 2, wherein the upper padding and the lower padding are formed of a thermoplastic elastomer.

4. The incontinence clamp of claim 2, wherein the upper padding and the lower padding each comprise a plurality of ridges formed on an outer surface.

5. The incontinence clamp of claim 1, wherein the upper guide and the lower guide are formed of a rigid polymer.

6. The incontinence clamp of claim 5, wherein the rigid polymer is acrylonitrile butadiene styrene.

7. The incontinence clamp of claim 1, wherein the connector comprises a plurality of connecting positions, wherein each of the connecting positions forms a different internal diameter of the incontinence clamp.

8. The incontinence clamp of claim 7, wherein one of the second ends comprises an interlocking tooth and the other of the second ends comprises a plurality of interlocking teeth, wherein the interlocking tooth is secured in between the plurality of interlocking teeth, releasably connecting the second ends together.

9. The incontinence clamp of claim 1, wherein the first side portion and the second side portion comprise a curved concave inner surface.

\* \* \* \* \*